United States Patent
Seed et al.

(10) Patent No.: US 6,719,977 B1
(45) Date of Patent: Apr. 13, 2004

(54) METHODS TO POTENTIATE CANCER THERAPIES

(75) Inventors: Brian Seed, Boston, MA (US); Rakesh K. Jain, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/601,919

(22) PCT Filed: Feb. 11, 1999

(86) PCT No.: PCT/US99/03083

§ 371 (c)(1),
(2), (4) Date: Dec. 21, 2000

(87) PCT Pub. No.: WO99/40929

PCT Pub. Date: Aug. 19, 1999

Related U.S. Application Data

(60) Provisional application No. 60/074,502, filed on Feb. 12, 1998.

(51) Int. Cl.$^7$ .......................... A61K 38/30; A61K 38/21
(52) U.S. Cl. .................. 424/198.1; 424/85.5; 530/303; 530/351; 514/2
(58) Field of Search ............................... 424/85.5, 85.4, 424/198.1; 530/351, 324, 303; 514/12, 21, 2

(56) References Cited

U.S. PATENT DOCUMENTS

| | | | |
|---|---|---|---|
| 4,656,249 A | 4/1987 | Tregear et al. ............... 530/324 |
| 5,128,126 A | * 7/1992 | Boniver ...................... 424/85.5 |
| 5,145,962 A | 9/1992 | Hudson et al. ............. 530/324 |
| 5,179,195 A | 1/1993 | Hudson et al. ............. 530/324 |
| 5,268,169 A | 12/1993 | Brandely et al. .......... 424/85.5 |
| 5,656,592 A | 8/1997 | Seed et al. ..................... 514/12 |
| 5,762,921 A | 6/1998 | Vehar ........................ 424/85.1 |

OTHER PUBLICATIONS

Sugiyama et al., Kurume Igakkai Zasshi, vol. 56, pp. 455–463, 1993.*
Hand et al., Anti–Cancer Drugs, vol. 6, pp. 77–82, 1995.*
Jaine, Sci. Amer., vol. 271, pp. 58–65, Jul. 1994.*
Curti, Critical Reviews in Oncology/Hematology, vol. 14, pp. 14–29, 1993.*
Ross et al. Immunology Today, vol. 11, No. 6, 1990.*
Siemen (in Rodent Tumor Models in Experimental Cancer Therapy, edited by Robert F. Kallman, published by Pergamon Press, 1987, pp. 12–15.*
Trott (in Rodent Tumor Models in Experimental Cancer Therapy, edited by Robert F. Kallman, published by Pergamon Press, 1987, pp. 6–11.*
Norrby et al., International Journal of Microcirculation: Clinical and Experimental, vol. 16, pp. 227–231, 1996.*

Fei et al., , Cyclic AMP Response to Recombinant Human Relaxin by Cultured Human Endometrial Cells—A Specific and High Throughput in Vitro Bioassay, 1990, Biochem. Biophys. Res. Comm. 170:214–222.
Ferrie et al., Development, Multiplexing, and Application of ARMS Tests for Common Mutations in the CFTR Gene, 1992, Am. J. Hum. Genet. 52:256–262.
Fodor et al., Light–Directed, Spatially Addressable Parallel Chemical Synthesis, 1991, Science 251:767–773.
Froyen et al., Bacterial Expression of a Single–Chain Antibody Fragment (SCFV) That Neutralizes the Biological Activity of Human Interferon–γ, 1993, Mol. Immunol. 30:805–812.
Gray and Goeddel, Structure of the Human Immune Interferon Gene, 1982, Nature 298:859–863.
Gray et al., Expression of Human Immune Interferon cDNA in *E. coli* and Monkey Cells, 1982, Nature 295:503–508.
Gunnersen et al., Characterization of Human Relaxin Gene Regulation in the Relaxin–Expressing Human Prostate Adenocarcinoma Cell Line LNCaP.FGC, 1995, J. Mol. Endocrinol. 15:153–166.
Guyer et al., How is the Human Genome Project doing, and what have we learned so far?, 1995, Proc. Natl. Acad. Sci. USA., 92:10841–10848.
Haley et al., Porcine Relaxin: Molecular Cloning and cDNA Structure, 1982, DNA 1:155:162.
Hand et al., Interferon (IFN)–α and IFN–γ in Combination With Methotrexate: in vitro Sensitivity Studies in Four Human Mesothelioma Cell Lines, 1995, Anti–Cancer Drugs 6:77–82.
Helmlinger et al., Solid Stress Inhibits the Growth of Multicellular Tumor Spheroids, 1997, Nature Biotechnol. 15:778–783.
Hudson et al., Relaxin Gene Expression in Human Ovaries and the Predicted Structure of a Human Preprorelaxin by Analysis of cDNA Clones, 1984, EMBO J., 3:2333–2339.
Hudson et al., Structure of a Genomic Clone Encoding Biologically Active Human Relaxin, 1983, Nature 301: 628–631.

(List continued on next page.)

*Primary Examiner*—Karen Cochrane Carlson
*Assistant Examiner*—Samuel W. Liu
(74) *Attorney, Agent, or Firm*—Clark & Elbing LLP

(57) ABSTRACT

Disclosed are methods for potentiating the anti-cancer properties of an anti-cancer therapy in a mammal by administering with the therapy a compound (such as relaxin or γ-IFN) that has a tissue tensile modulus-reducing property, an ability to reduce the interstitial viscosity of the cancer, an ability to increase the hydraulic conductance of the cancer, or an ability to increase collagen turnover or decrease collagen formation at or near the cancer, where the therapy and the compound are administered at dosages which together are sufficient to destroy, slow, or arrest the cancer. Also disclosed is a method for treating cancer in a mammal involving the administration of relaxin and/or γ-IFN peptides and an anti-cancer therapy to the mammal, where the peptides and the therapy are administered at dosages which together are sufficient to destroy, slow, or arrest the cancer.

8 Claims, No Drawings

OTHER PUBLICATIONS

Iigo et al., Synergistic Antitumor Effects of Carboplatin and Interferons on Hepatic Metastases of Colon Carcinoma 26 and M5076 Reticulum Cell Sarcoma, 1993, Jpn. J. Cancer Res., 84:794–799.

Jordan et al., A march of genetic maps, 1996, Nature 380:111–112.

Kopp et al., Immunomodulatory Effects of Interferon–γ in Patients with Metastatic Malignant Melanoma, 1993, J Immunotherapy 13:181–190.

Kozal et al., Extensive polymorphisms observed in HIV–1 clade B protease gene using high–density oligonucleotide arrays, 1996, Nature Medicine 2:753–759.

Kramer et al., Increase in Cyclic AMP Levels by Relaxin in Newborn Rhesus Monkey Uterus Cell Culture, 1990, In Vitro Cell. Dev. Biol. 26:647–656.

Li et al., Direct electrophoretic detection of the allelic state of single DNA molecules in human sperm by using the polymerase chain reaction, 1990, Proc. Natl. Acad. Sci. USA 87:4580–4584.

Bolinger and Taeubel, Recombinant Interferon gamma for Treatment of Chronic Granulomatous Disease and Other Disorders, 1992, Clin. Pharm., 11:834–850.

Bryant–Greenwood, D. G., At the Cutting Edge, The Human Relaxins: Consensus and Dissent, 1991, Molecular and Cellular Endocrinology 79:C125–C132.

Bullesbach and Schwabe, Naturally Occuring Porcine Relaxins and Large–Scale Preparation of the B29 Hormone, 1985, Biochemistry 24:7717–7722.

Bullesbach and Schwabe, Preparation and Properties of Porcine Relaxin Derivatives Shortened in the Amino Terminus of the A Chain, 1986, Biochemistry 25:5998–6004.

Cha et al., Mismatch Amplification Mutation Assay (MAMA): Application to the c–H–ras Gene, 1992, PCR Methods & Applications 2:14–20.

Chang et al., Multiplex Mutagenically Separated PCR: Diagnosis of β–Thalassemia and Hemoglobin Variants, 1997, Biotechniques 22:520–527.

Derynck et al., Expression of the Human Interferon–γ cDNA in Yeast, 1983, Nucleic Acids Res. 11: 1819–1837.

Derynck et al., Human Interferon γ is encoded by a Single Class of mRNA, 1982, Nucleic Acids Res. 10: 3605–3615.

Devos et al., Molecular Cloning of Human Immune Interferon cDNA and Its Expression in Eukaryotic Cells, 1982, Nucleic Acids Res. 10:2487–2501.

Devos et al., The use of random amplified polymorphic DNA markers in wheat, 1992, Theor. Appl. Genet. 84:567–572.

Dietrich et al., A Genetic Map of the Mouse Suitable for Typing Intraspecific Crosses, 1992, Genetics 131:423–447.

Dietrich et al., Mapping the mouse genome: Current status and future prospects, 1995, Proc. Natl. Acad. Sci. USA 92:10849–10853.

Lipshutz et al., Using Oligonucleotide Probe Arrays To Access Genetic Diversity, 1995, Biotechniques 19:442–447.

Nishi et al., Cloning and Expression of a Novel Variant of Human Interferon–γ cDNA, 1985, J. Biochem. 97:153–159.

Park et al., Effects of Gamma Interferon on the Growth of Ascitic Sarcoma–180 and the Radioprotection of the Jejunal Mucosa in Irradiated Mice, 1994, Katollik Taehak Uihakpu Nonmunjip 47:1821–35, abstract.

Pease et al., Light–generated oligonucleotide arrays for rapid DNA sequence analysis, 1994, Proc. Natl. Acad. Sci. USA 91:5022–5026.

Petruska et al., Comparison between DNA melting thermodynamics and DNA polymerase fidelity, 1988, Proc. Natl. Acad. Sci. USA 85:6252–6256.

Riedy et al., Excess of non–parental bands in offspring from known primate pedigrees assayed using RAPD PCR, 1992, Nucleic Acids Research 20:918.

Sarkar et al., Characterization of Polymerase Chain Reaction Amplification of Specific Alleles, 1990, Analytical Biochemistry 186:64–68.

Schena et al., Parallel human genome analysis: Microarray–based expression monitoring of 1000 genes, 1996, Proc. Natl. Acad. Sci. USA 93:10641–10619.

Schena et al., Quantitative Monitoring of Gene Expression Patterns with a Complementary DNA Microarray, 1996, Science 270:467–470.

Seelig et al., Evidence for a Polypeptide Segment at the Carboxyl Terminus of Recombinant Human γ Interferon Involved in Expression of Biological Activity, 1988, Biochemistry 27:1981–1987.

Southern et al., DNA chips: analysing sequence by hybridization to oligonucleotides on a large scale, 1996, TIG 12:110–115.

Sugiyama, Experimental Research for Anti–Tumor Effect of Interferon, 1993, Kurume Igakkai Zasshi, 56:455–63.

Taya et al., Cloning and Structure of the Human Immune Interferon–γ Chromosomal Gene, 1982, EMBO J., 1:953–958.

Vandenbroeck et al., Engineering by PCR–Based Exon Amplification of the Genomic Porcine Interferon–Gamma DNA for Expression in *Escherichia Coli*, 1991, Biochem. Biophys. Res. Commun. 180:1408–1415.

Vu et al., Recombinant Porcine Prorelaxin Produced in Chinese Hamster Ovary Cells is Biologically Active, 1993, Life Sci. 52:1055–1061.

Wenham et al., Analysis of Apolipoprotein E Genotypes by the Amplification Refractory Mutation System, 1991 Clin. Chem. 382:241–244.

Williams et al., DNA polymorphisms amplified by arbitrary primers are useful as genetic markers, 1990 Nucleic Acids Research 24:380–385.

Winslow et al., Purification and Structure of Human Pregnancy Relaxin from Corpora Lutea, Serum and Plasma, 1989 Proc. 71th Meeting of Endocrine Society 889 Abstract.

Ackland et al., "Nonsteroidal Signals Originating in the Gonads," *Physiological Reviews* 73(2):731 and 741–743 (1992).

Calguneri et al., "Changes In Joint Laxity Occurring During Pregnancy," *Annals of the Rheumatic Diseases* 41:126–128 (1982).

Genentech Company Report, Oct. 14, 1987, Abstract.

Genentech, Inc., Annual Report, 1992.

Horowitz, "Role of Nitrates in Unstable Angina Pectoris," *The American Journal of Cardiology* 70:64B–71B, (1992).

Hudson et al., "Molecular Cloning And Characterization of cDNA Sequences Coding for Rat Relaxin," *Nature* 291:127–131 (1981).

Jones et al., "Relaxin Increases Blood Pressure and Vasopressin Levels in Anaesthetized Rats," *Physiological Society* p. 37P (1986).

Kakouris et al., "Relaxin: More Than Just a Hormone of Pregnancy," *TiPS* 14:4–6, (1993).

Kibblewhite et al., "The Effect of Relaxin on Tissue Expansion," *Arch. Otolaryngol. Head Neck Surg.* 118:153–156 (1992).

MacLennan et al., "Serum Relaxin and Pelvic Pain of Pregnancy," *The Lancet* p.243–245 (1986).

Maclennan, "The Role of the Hormone Relaxin in Human Reproduction and Pelvic Girdle Relaxation," *Scand. J. Rheumatology* 88:7–15 (1991).

Östgaard et al., "Previous Back Pain and Risk of Developing Back Pain in a Future Pregnancy," *Spine* 16:432–436 (1991).

Östgaard et al., "Prevalence of Back Pain in Pregnancy," *Spine* 16:549–552 (1991).

PR Newswire, Apr. 25, 1983, Abstract.

Saugstad, "Persistent Pelvic Pain and Pelvic Joint Instability," *European Journal of Obstetrics & Gynecology and Reproductive Biology* 41:197–201 (1991).

Sherwood et al., "Purification and Characterization of Porcine Relaxin," *Archives Of Biochemistry And Biophysics* 160:185–196 (1974).

St. Louis et al., "Chronic Decrease of Blood Pressure by Rat Relaxin in Spontaneously Hypertensive Rats," *Life Sciences* 37:1351–1357.

Walsh et al., "Use of an Octadecylsilica Purification Method Minimizes Proteolysis During Isolation of Porcine and Rat Relaxins," *Endocrinology* 107(4):1258–1260 (1980).

\* cited by examiner

METHODS TO POTENTIATE CANCER THERAPIES

This application claims the benefit of Provisional application Ser. No. 60/074,502, filed Feb. 12, 1998.

BACKGROUND OF INVENTION

This invention relates to anti-cancer therapy, particularly for the treatment of solid tumors.

Cancer accounts for one fifth of the total mortality in the United States and is the second leading cause of death. One effective anti-cancer therapy is chemotherapy. However, in the treatment of solid tumors (e.g., tumors in the lung, colon, and breast), efficient treatment is hindered by the difficulty in penetrating the tumor mass with anti-cancer agents (Jain, Sci. Amer. 271: 58–65, 1994). Hence, the identification of a means by which to facilitate the delivery of therapeutic agents to the cancer site would enhance the effectiveness of anti-cancer therapies.

SUMMARY OF THE INVENTION

We have discovered methods and reagents for increasing the sensitivity of cancers to therapy, and particularly chemotherapy. These methods and reagents are useful in treating cancers, particularly solid tumors.

Accordingly, in a first aspect, the invention features a method for treating a cancer in a mammal that involves administering relaxin and an anti-cancer therapy to the mammal, the relaxin and the anti-cancer therapy being administered at dosages which together are sufficient to destroy, slow, or arrest the cancer. In various preferred embodiments of this aspect of the invention, the relaxin is administered either prior to the administration of the anti-cancer therapy or simultaneously with the administration of the anti-cancer therapy. In another preferred embodiment, the method further involves administration of γ-interferon.

In a second aspect, the invention features a method for treating a cancer in a mammal that involves administering γ-interferon and an anti-cancer therapy to the mammal, the γ-interferon and the anti-cancer therapy being administered at dosages which together are sufficient to destroy, slow, or arrest the cancer. In various preferred embodiments of this aspect of the invention. the γ-interferon is administered either prior to the administration of the anti-cancer therapy or simultaneously with the administration of the anti-cancer therapy. In another preferred embodiment, the method further involves administration of relaxin.

In preferred embodiments of both the first and second aspects of the invention, the anti-cancer therapy includes a biotherapeutic agent, for example, a chemotherapeutic agent. And in other preferred embodiments, the mammal is a human; and the cancer is a solid tumor, for example, a solid tumor in a tissue selected from the group consisting of brain, kidney, liver, nasopharyngeal cavity, thyroid, skin, central nervous system, ovary, breast, prostate, colon, rectum, uterus, cervix, endometrium, lung, bladder, pancreas, and lymph node.

In related aspect, the invention features a method for treating a cancer in a mammal that involves administering to the mammal a tissue tensile modulus-reducing compound and an anti-cancer therapy, the compound and the anti-cancer therapy being administered at dosages which together are sufficient to destroy, slow, or arrest the cancer.

In yet another related aspect, the invention features a method for treating a cancer in a mammal that involves administering to the mammal a compound that increases the hydraulic conductance of the cancer and an anti-cancer therapy, the compound and the anti-cancer therapy being administered at dosages which together are sufficient to destroy, slow, or arrest the cancer.

In a final related aspect, the invention features a method for treating a cancer in a mammal that involves administering to the mammal a compound that increases collagen turnover or decreases collagen formation at or near the cancer and an anti-cancer therapy, the compound and the anti-cancer therapy being administered at dosages which together are sufficient to destroy, slow, or arrest the cancer.

In various preferred embodiments of the above related aspects, the anti-cancer therapy includes a biotherapeutic agent, for example, a chemotherapeutic agent; the mammal is a human; the cancer is a solid tumor; and the compound is either relaxin or γ-interferon, or both.

As used herein, by "cancer" or "neoplasm" is meant any abnormal proliferation of cells, which may be benign or malignant, and which includes solid tumors. Solid tumors may occur in a variety of tissues including, without limitation, the brain, kidney, liver, nasopharyngeal cavity, thyroid, skin, central nervous system, ovary, breast, prostate, colon, rectum, uterus, cervix, endometrium, lung, bladder, pancreas, and lymph node.

By "anti-cancer therapy" is meant any therapy that destroys a cancer cell, or slows, arrests, or reverses the growth of a cancer cell. Anti-cancer therapies include, without limitation, radiation therapy (radiotherapy), chemotherapy, or a combination of these therapies.

By "chemotherapy" is meant the use of a chemical agent to destroy a cancer cell, or to slow, arrest, or reverse the growth of a cancer cell.

By "biotherapeutic agent" is meant a substituted or unsubstituted peptide, polypeptide, virus cell, glycan, or combination thereof, which may be used to destroy a cancer cell, or to slow, arrest, or reverse the growth of a cancer cell.

By "chemotherapeutic agent" is meant a chemical that may be used to destroy a cancer cell, or to slow, arrest, or reverse the growth of a cancer cell. Chemotherapeutic agents include, without limitation, asparaginase, bleomycin, busulfan carmustine (commonly referred to as BCNU), chlorambucil, cladribine (commonly referred to as 2-CdA), irinotecan (CPT-11), cyclophosphamide, cytarabine (commonly referred to as Ara-C), dacarbazine, daunorubicin, dexamethasone, doxorubicin (commonly referred to as Adriamycin), etoposide, fludarabine, 5-fluorouracil (commonly referred to as 5FU), hydroxyurea, idarubicin, ifosfamide, interferon-α (native or recombinant), levamisole, lomustine (commonly referred to as CCNU), mechlorethamine (commonly referred to as nitrogen mustard), melphalan, mercaptopurine, methotrexate, mitomycin, mitoxantrone, paclitaxel, pentostatin, prednisone, procarbazine, tamoxifen, taxol-related compounds, 6-thiogaunine, topotecan, vinblastine, and vincristine.

By "responsive" is meant that a cell is destroyed by an anti-cancer therapy, or that the growth of a cell is slowed, arrested, or reversed by an anti-cancer therapy. The growth may be measured by any standard technique including, for example, cell count, measurement with calipers, or weight. Preferably, the growth of the cancer is reversed such that the cancer is at least 50% smaller than the cancer prior to therapy. Most preferably, the cancer is destroyed by the therapy.

By a "tissue tensile modulus-reducing compound" is meant a compound that reduces the tensile modulus (i.e., the Young's modulus, or the coefficient of the strain in the linear stress to strain relation) of tissue deformed by the presence of a cancer.

Other features and advantages of the invention will be apparent from the following detailed description and from the claims.

DETAILED DESCRIPTION

A significant obstacle to the delivery of anti-cancer agents, and particularly chemotherapeutic agents, to solid tumors is the tumor hydrostatic environment. The tumor core has a high internal pressure, and the tumor interstitium is highly viscous. Together these effects form a barrier to conduction of small and large molecules from the plasma into the tumor. The high central pressure in the tumor is resisted by elastic forces generated in the surrounding tissue and from within the tumor itself. Hence, the tumor generates pressure, presumably by uncontrolled proliferation, which acts both upon the tumor constituents and the surrounding normal but deformed tissue. At equilibrium, the elastic forces and the pressure balance, and the tumor neither expands nor shrinks on a rapid time scale.

The elastic forces that arise by dislocation or stretching of tissue have their origin in the strain (extension or compression) of both intracellular cytoskeletal elements and extracellular matrix components. Together their perturbation away from an equilibrium state produces a stress (force) which is usually taken to be linear in the strain. Little is known at present about the relative contribution of intracellular and extracellular components to the Young's modulus (that is, the coefficient of the strain in the linear stress-strain relation) of tissue deformed by the presence of a tumor (Helmlinger et al., Nature Biotechnol. 15: 778–783, 1997).

To reduce this tissue tensile modulus of solid tumors, the present invention involves the administration of relaxin and/or γ-interferon (γ-IFN) peptides, and thereby improves anti-cancer therapeutic approaches. In the setting of neoplasia, a reduction in the tissue tensile modulus might be expected to facilitate tumor growth by decreasing mechanical resistance to cellular proliferation and spread. Although superficially this would be considered undesirable, in the context of chemotherapy, decreased tumor pressure and facilitated tumor growth are expected to enhance the cytotoxic potential of existing anti-neoplastic agents, nearly all of which are directed at killing rapidly proliferating cells. With respect to relaxin, it has been demonstrated that in at least one experimental setting, namely, the stretching of skin by an implanted subcutaneous balloon, that the pressure-volume relationship for the expansion of the fluid-filled balloon could be altered by the infusion of relaxin. In this case, the administration of relaxin decreased the resistance to balloon expansion. Thus relaxin has, over a period of time, the capacity to decrease the modulus of skin and underlying connective tissue.

High tumor interstitial viscosity is another important consideration for the effective delivery of chemotherapeutic agents. In general, the diffusion coefficient of molecules in liquids is inversely related to the viscosity of the solvent. Increasing viscosity thus retards diffusion of plasma-borne drugs into the tumor interstitium. A recent unexpected finding has been that interstitial viscosity is strongly influenced by the presence of collagen, and that infusion of collagenase dramatically facilitates penetration of small and large molecules into a tumor.

Related to the high interstitial viscosity of solid tumors is a low hydraulic conductivity. This latter measure incorporates both diffusive and convective flow, and is a measure of total fluid conductance. Resistance to convective flow can be thought of as arising from macroscopic effects which limit the cross-section available to flow and induce flow resistance through propagation of the influence of the static boundary layer at the solid-fluid interface. Collagenase treatment also increases hydraulic conductance, underscoring the importance of the matrix contribution to bulk fluid flow.

The methods of the present invention further facilitate the delivery of anti-cancer therapeutics by also reducing interstitial viscosity and increasing hydraulic conductance of tumors through a decrease in the presence and/or concentration of collagen. In animal models, relaxin has been shown to prevent the formation of fibrotic capsules surrounding impenetrable foreign bodies, the accumulation of collagen within implanted sponges, and the parenchymal fibrosis that accompanies oxidative pulmonary damage induced by the chemotherapeutic agent bleomycin. And γ-interferon (γ-IFN), a pleiotypic cytokine produced by helper T cells, has been shown, in a number of experimental settings, to inhibit fibroblast proliferation and associated matrix deposition, actions that are consistent with the ability of γ-IFN to antagonize production of basic fibroblast growth factor (bFGF). In addition, because the mechanisms of action of these peptides differ, the combination of relaxin and γ-IFN are likely to have more potent anti-fibrotic action than that produced by either agent alone.

The present invention makes use of these characteristics of relaxin and γ-IFN to potentiate anti-cancer therapies. Because both relaxin and γ-IFN act as anti-fibrotic agents which have the capacity to reduce collagen and matrix accumulation, and to accelerate matrix turnover, administration of these peptides are useful for reducing tumor pressure and decreasing interstitial viscosity, effects which facilitate the penetration of cytotoxic agents into tumors. Thus, the delivery of relaxin, γ-IFN, or relaxin plus γ-IFN, may be utilized to potentiate the effects of anti-cancer agents. Of the two peptides, relaxin is expected to affect existing collagenous matrix, whereas γ-IFN is likely to retard the formation of new tumor stroma from existing fibroblasts. As a result, the action of relaxin is likely to be more rapid.

For cancer therapy, and particularly chemotherapy, these anti-fibrotic peptide hormones are likely to be most effective if provided in advance of the anti-neoplastic agent, to condition the tumor bed for more effective drug delivery. The timing of the relaxin and/or γ-IFN treatment should be adjusted to optimize tumor susceptibility without allowing excessive tumor growth. Because relaxin is known to exert its effects relatively rapidly (essentially immediately for protection against an acute fibrotic insult), a preferable treatment regimen involves initiation of relaxin and/or γ-IFN treatment within a few days prior to the first round of therapy and continuation of one or both of these peptides for the duration of the therapy.

CHEMOTHERAPEUTIC AGENTS

Although the administration of relaxin and/or γ-IFN may be used with any anti-neoplastic agent, a preferred treatment regimen according to the invention involves chemotherapy, or the use of chemical agents to destroy cancer cells. Several classes of chemotherapeutic agents are available, and many may be used in combination. Accordingly, it will be understood that where "a chemotherapeutic agent" is referred to in accordance with the present invention, a combination of two or more such agents may be employed. The agent(s) may be introduced into the body as a whole, or their administration may be concentrated at the tumor site.

Useful chemotherapeutic agents include, without limitation, alkylating agents, nitrosoureas, anti-metabolites, plant alkaloids, antitumor antibiotics, and steroid hormones. Each agent is categorized according to its effect on the cell cycle and cell chemistry. Alkylating agents, for example, are useful chemotherapeutics that kill cells by directly attacking DNA, and may be used, according to the invention, in the treatment of, for example, chronic leukemias, Hodgkin's disease, lymphomas, and certain carcinomas of the lung, breast, prostate, and ovary. One commonly used alkylating agent is cyclophosphamide.

Nitrosourea drugs are also useful chemotherapeutics of the invention which, being able to cross the blood-brain barrier, may be used, for example, to treat brain tumors, as well as lymphomas, multiple myeloma, and malignant melanoma. Drugs of this category, to which carmustine (BCNU) and lomustine (CCNU) belong, act similarly to akylating agents and, additionally, inhibit changes necessary for DNA repair.

Another category of chemotherapeutics useful in the present invention is the anti-metabolite category, which includes drugs that block cell growth by interfering with certain activities during the "S" phase of the cell cycle, usually DNA synthesis. Once ingested into the cell, anti-metabolites halt normal development and reproduction, and are useful, for example, for the treatment of acute and chronic leukemias, choriocarcinoma, and tumors of the gastrointestinal tract, breast, and ovary. Examples of commonly used anti-metabolites are 6-mercaptopurine and 5-fluorouracil (5FU).

Plant (vinca) alkaloids are plant-derived anti-tumor agents which may also be exploited in the methods of the invention, and include vincristine and vinblastine. These agents, which act specifically by blocking cell division during mitosis, are commonly used in the treatment of acute lymphoblastic leukemia, Hodgkin's and non-Hodgkin's lymphomas, neuroblastomas, Wilms' tumor, and cancers of the lung, breast, and testes.

Antitumor antibiotics are another diverse group of compounds that may be used in the methods of the invention and that, in general, act by binding with DNA and preventing RNA synthesis. These agents may be used for the treatment of a variety of cancers, and include doxorubicin (Adriamycin), mitomycin-C, and bleomycin.

Steroid hormones, or hormone antagonists, may also be used as chemotherapeutic agents, given their abilities to modify the growth of certain hormone-dependent cancers. This class includes adrenocorticosteroids, estrogens, anti-estrogens, progesterones, and androgens. One example of a steroid hormone antagonist is tamoxifen, a drug used for estrogen-dependent breast cancer.

In addition to the above, any other chemotherapeutic agent may be used in the methods of the invention, including other anti-neoplastic agents whose mechanisms of action do not permit broad categorization.

Systemic Administration of Relaxin and γ-IFN

For use as enhancers of anti-cancer therapeutics, relaxin and γ-IFN may be administered systemically, for example, formulated in a pharmaceutically-acceptable buffer such as physiological saline. Preferable routes of administration include, for example, intravenous, subcutaneous, intramuscular or intradernal injections which provide continuous, sustained levels of the drug in the patient. In other preferred routes of administration, relaxin and/or γ-IFN may be given to a patient by injection of a slow release preparation, slowly dissociating polymeric form, or crystalline form; this sort of sustained administration may follow an initial delivery of the drug by more conventional routes (for example, those described above). Alternatively, relaxin and γ-IFN may be administered using an infusion pump, thus allowing a precise degree of control over the rate of drug release, or through instillation of relaxin and γ-IFN in the nasal passages in a similar fashion to that used to promote absorption of insulin. Finally, as an alternative to nasal transmucosal absorption, relaxin and γ-IFN may be delivered by aerosol deposition of a powder or solution into the lungs.

Local Administration of Relaxin and γ-IFN

Relaxin and γ-IFN may also be administered locally to achieve substantial chemotherapy-enhancing outcomes. Since the desired action of the agent is generally upon a circumscribed mass of tissue proximal to a specific cancer, delivery of the peptide by means which promote high local concentrations in the vicinity of the cancer may be especially desirable. For this reason, injection of the agent into tissue sites adjacent to, or upstream of the draining circulation of, the affected site is preferable. Alternatively, in conditions involving deep organ structures, for example, in the displacement of tissue by invasive tumors, implantation of sustained release formulations of relaxin and/or γ-IFN (such as osmotic pumps or erodable polymeric compositions impregnated with the hormone) near the affected tumor site may be preferred.

Administration of Chemotherapeutic Agents with Relaxin and γ-IFN

The most common routes of administration for chemotherapy are oral, intravenous, and intramuscular. More recently, other methods have been used to increase the local concentration of chemotherapeutic agents at a tumor site. For example, if the cancer occurs in an arm or leg, chemotlherapy may be administered by arterial perfusion, delivering the chemotherapeutic agent directly into the bloodstream of the arm or leg where the cancer is found. Chemotherapy can also be administered directly into a specific cavity (intracavitary), the abdomen (intraperitoneal), the lung (intrapleural), or the central nervous system (intrathecal), or may be applied directly to the skin (topical). If desired, relaxin and/or γ-IFN may be administered by the same route as the chemotherapeutic agent, even if relaxin and/or γ-IFN and the chemotherapeutic agent are not administered simultaneously.

Relaxin

Relaxin, for either systemic or local administration, may be obtained from Connectics Corporation (Palo Alto, CA), or may be synthesized either by standard techniques of recombinant polypeptide production (see, e.g., Ausubel et al., *Current Protocols in Molecular Biology*, John Wiley & Sons, New York, 1997; Sambrook et al., *Molecular Cloning, A Laboratory Manual*, 2nd ed., Cold Spring Harbor Press, Cold Spring Harbor, N.Y., 1989) or by peptide synthesis (e.g., by the methods described in *Solid Phase Peptide Synthesis*, 2nd ed., 1984 The Pierce Chemical Co., Rockford, Ill.). Relaxin gene and peptide sequences are provided, e.g., in Hudson et al., Nature 301:628–631, 1983; Hudson et al., EMBO J. 3:2333–2339, 1984; and Gunnersen et al., J. Mol. Endocrinol. 15: 153–166, 1995.

Generally, the relaxin polypeptide native to a species will be preferred for therapeutic administration. However, relaxin fragments or analogs shown to be functional, e.g., in the bioassays of Fei et al. (Biochem. Biophys. Res. Comm. 170:214–222, 1990) and Kramer et al. (In Vitro Cell. Dell. Biol. 26:647–656, 1990), and in the mouse pubic symphysis assay (Bullesbach and Schwabe, Biochemistry 25:5998–6004, 1986) are also useful in the invention. Particularly preferred relaxin fragments include the B29 relaxin fragment described by Winslow et al. (Proc. 71st Meeting of Endocrine Society 889 Abstract, 1989). Bryant-Greenwood, D. G., Molecular and Cellular Endocrinology 79: C125–C132, 1991), and Bullesbach and Schwabe (Biochemistry 24: 7717–7722,1985). Particularly preferred relaxin analogs include polypeptides which differ from a native relaxin polypeptide only by conservative amino acid substitutions, for example substitution of one amino acid for another of the same class (e.g., valine for glycine, arginine for lysine, aspartic acid for glutamic acid, etc.). Other preferred analogs include relaxin polypeptides which are modified for the purpose of increasing peptide stability; such analogs may contain, e.g., one or more desaturated peptide bonds or D-amino acids in the peptide sequence or may be formulated as cyclized peptide molecules. Finally, a prorelaxin polypeptide (see, e.g., Hudson et al., EMBO J. 3:2333, 1984; and Vu et al., Life Sci. 52:1055, 1993) may be administered as a chemotherapy-enhancing reagent according to the invention.

γ-Interferon (γ-IFN)

γ-IFN, for either systemic or local administration, may also be obtained from any commercially available source (e.g., Sigma-Aldrich Chemical Co., St, Louis, Mo.), or may be synthesized either by standard techniques of recombinant polypeptide production or by peptide synthesis, as described above. γ-IFN gene and peptide sequences are provided, e.g., in Taya et al., EMBO J. 1: 953–958, 1982; Gray et al., Nature 295: 503–508, 1982; Gray and Goeddel, Nature 298: 859–863, 1982; Devos et al., Nucleic Acids Res. 10: 2487–2501, 1982; Derynck et al., Nucleic Acids Res. 10: 3605–3615, 1982; Gray and Goeddel, Basic Life Sci. 23: 35–61,1983; Derynck et al., Nucleic Acids Res. 11: 1819–1837, 1983; Nishi et al., J. Biochem. 97: 153–159, 1985; and GenBank Accession No. X87308.

Generally, the γ-IFN polypeptide native to a species will be preferred for therapeutic administration. However, γ-IFN fragments or analogs shown to be functional (using e.g., a γ-IFN functional assay such as those described by Froyen et al., Mol Immunol 30:805–812, 1993; and Seelig et al., Biochemistry 27:1981–1987, 1988) may also be administered as chemotherapy-enhancing reagents according to the invention. Preferred γ-IFN analogs include polypeptides which differ from a native γ-IFN polypeptide only by conservative amino acid substitutions, and γ-IFN polypeptides which are modified for the purpose of increasing peptide stability.

Dosages of Relaxin and γ-IFN

Relaxin is administered systemically at a dosage that provides an enhancement of the cancer cell-inhibiting effects of a chemotherapeutic agent. Dosages of relaxin are typically administered to result in a blood serum concentration that is between 0.1–100 nanograms/ml, preferably between 1–10 nanograms/ml, and may be administered with the appropriate dosage of the chemotherapeutic agent with or without γ-IFN. Because administration of the relaxin polypeptide may promote loosening of connective tissues, it may be desirable, where possible, to encourage muscular development through physical therapy to counteract any excessive loosening observed during the course of relaxin treatment.

γ-IFN is also administered systemically at a dosage that provides an enhancement of the cancer cell-inhibiting effects of a chemotherapeutic agent. Dosages of γ-IFN are typically between 0.01 and 10 mg/sq. meter body surface area (Kopp et al., J Immunother. 13: 181–190, 1993; Bolinger and Taeubel, Clin. Pharm. 11: 834–850, 1992), and may be administered with a chemotherapeutic agent with or without co-administration of relaxin.

Relaxin and/or γ-IFN may be administered simultaneously with the chemotherapeutic agent or, as described above, a few days prior to the initiation of administration of the chemotherapeutic agent. Where local administration schemes are employed, the concentrations of relaxin in the affected tissue may substantially exceed the levels described above.

Other Embodiments

The methods of the invention may be used to potentiate anti-cancer therapies in any mammal, for example, humans, domestic pets, or livestock. Where a non-human mammal is treated, the relaxin and/or γ-IFN employed is preferably specific for that species (e.g., for pigs, see Haley et al., DNA 1: 155, 1982; and Vandenbroeck et al, Biochem. Biophys. Res. Commun. 180:1408–1415, 1991)

All publications and patent applications mentioned in this specification are herein incorporated by reference to the same extent as if each independent publication or patent application was specifically and individually indicated to be incorporated by reference.

Other embodiments are within the claims.

What is claimed is:

1. A method of increasing the sensitivity of a mammalian solid tumor to an anti-cancer therapy, said method comprising administering to a mammal having a solid tumor relaxin and an anti-cancer therapy, said relaxin being administered at a dosage that increases the penetration of said anti-cancer therapy into said solid tumor.

2. The method of claim 1, wherein said anti-cancer therapy comprises a biotherapeutic agent.

3. The method of claim 1, wherein said anti-cancer therapy comprises a chemotherapeutic agent.

4. The method of claim 1, wherein said relaxin is administered prior to the administration of said anti-cancer therapy.

5. The method of claim 1, wherein said relaxin is administered simultaneously with the administration of said anti-cancer therapy.

6. The method of claim 1, wherein said method further comprises administration of γ-interferon.

7. The method of claim 1, wherein said mammal is a human.

8. The method of claim 1, wherein said solid tumor is in a tissue selected from the group consisting of brain, kidney, liver, nasopharyngeal cavity, thyroid, skin, central nervous system, ovary, breast, prostate, colon, rectum, uterus, cervix, endometrium, lung, bladder, pancreas, and lymph node.

* * * * *

UNITED STATES PATENT AND TRADEMARK OFFICE
CERTIFICATE OF CORRECTION

PATENT NO. : 6,719,977 B1
DATED : April 13, 2004
INVENTOR(S) : Seed et al.

It is certified that error appears in the above-identified patent and that said Letters Patent is hereby corrected as shown below:

Column 1,
Line 5, after "Feb. 1, 1998." insert the following paragraph:
-- This invention was made with Government support under Grant Number CA56591 awarded by the National Institutes of Health. The Government has certain rights in this invention. --

Column 2,
Line 55, replace "6-thiogaunine" with -- 6-thioguanine --.

Column 5,
Line 21, replaec "akylating" with -- alkylating --; and
Line 67, replace "intradernal" with -- intradermal --.

Column 6,
Line 29, replace "erodable" with -- erodible --;
Line 40, replace "leg." with -- leg, --; and
Lines 40-41, replace "chemotlherapy" with -- chemotherapy --.

Signed and Sealed this

Tenth Day of August, 2004

JON W. DUDAS
*Acting Director of the United States Patent and Trademark Office*